United States Patent
Tabur et al.

(10) Patent No.: US 11,350,958 B2
(45) Date of Patent: Jun. 7, 2022

(54) FULL-CIRCUMFERENTIAL TISSUE RESECTIONING

(71) Applicant: Boston Scientific Scimed, Inc., Maple Grove, MN (US)

(72) Inventors: Peter Tabur, Hollis, NH (US); Matthew R. Jagelski, Marlborough, MA (US); George W. Duval, Sudbury, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 206 days.

(21) Appl. No.: 16/408,897

(22) Filed: May 10, 2019

(65) Prior Publication Data

US 2019/0343544 A1 Nov. 14, 2019

Related U.S. Application Data

(60) Provisional application No. 62/670,015, filed on May 11, 2018.

(51) Int. Cl.
*A61B 17/32* (2006.01)
*A61B 17/00* (2006.01)

(52) U.S. Cl.
CPC ........ *A61B 17/320016* (2013.01); *A61B 17/00234* (2013.01); *A61M 2210/106* (2013.01); *A61M 2210/1064* (2013.01)

(58) Field of Classification Search
CPC ...... A61B 17/320016; A61B 17/00234; A61B 17/11; A61B 17/1114; A61B 2017/00269; A61B 2017/00296; A61B 2017/00353; A61B 2017/1103; A61B 2017/1107; A61B 2017/111; A61B 2017/320024; A61B 2017/1121; A61B 2017/1132; A61B 2017/00278; A61B 2017/00349; A61B 17/32053; A61B 17/32075; A61M 2210/1064; A61M 2210/106
See application file for complete search history.

(56) References Cited

U.S. PATENT DOCUMENTS

| 4,766,898 A | * | 8/1988 | Hardy | A61B 17/1114 606/154 |
| 5,250,058 A | * | 10/1993 | Miller | A61B 17/11 24/615 |
| 5,411,508 A | * | 5/1995 | Bessler | A61B 17/1114 227/179.1 |

(Continued)

*Primary Examiner* — Ryan J. Severson
(74) *Attorney, Agent, or Firm* — Seager, Tufte & Wickhem, LLP

(57) ABSTRACT

Apparatuses, devices, and methods for performing endoscopic tissue resectioning in the gastrointestinal tract are disclosed. In some embodiments, a tissue resectioning device may include first and second scaffolds each arranged in a tubular configuration. The tissue resectioning device may further include a hook tool engageable with the first scaffold and/or the second scaffold to bias the scaffolds to engage a target section of tissue between the first scaffold and the second scaffold. The hook tool may also engage the section of tissue to pull the section of tissue into the path of a cutting edge of each of the first and second scaffolds. In some embodiments, the tissue resectioning device is provided over a scope, which extends within a lumen of an overtube.

19 Claims, 12 Drawing Sheets

(56) References Cited

U.S. PATENT DOCUMENTS

| | | | |
|---|---|---|---|
| 5,425,738 A * | 6/1995 | Gustafson | A61B 17/1114 |
| | | | 606/151 |
| 6,666,873 B1 * | 12/2003 | Cassell | A61B 17/0643 |
| | | | 606/153 |
| 7,338,505 B2 | 3/2008 | Belson | |
| 8,590,764 B2 | 11/2013 | Hartwick et al. | |
| 8,911,458 B2 | 12/2014 | Bassan et al. | |
| 9,155,539 B2 | 10/2015 | Gronberg et al. | |
| 9,295,470 B2 | 3/2016 | Baur et al. | |
| 9,743,931 B2 | 8/2017 | Grönberg | |
| 9,820,746 B2 | 11/2017 | Imran | |
| 10,130,502 B2 | 11/2018 | Chamorro et al. | |
| 10,307,280 B2 | 6/2019 | Zeiner et al. | |
| 10,420,665 B2 | 9/2019 | Sharma et al. | |
| 10,548,753 B2 | 2/2020 | Rousseau | |
| 2011/0011916 A1 * | 1/2011 | Levine | A61B 17/115 |
| | | | 227/179.1 |
| 2011/0098630 A1 * | 4/2011 | Gagner | A61F 2/04 |
| | | | 604/9 |
| 2012/0215238 A1 * | 8/2012 | Borghi | A61B 17/11 |
| | | | 606/153 |
| 2015/0245839 A1 * | 9/2015 | Wirtel, III | A61B 17/0643 |
| | | | 606/153 |
| 2017/0281181 A1 | 10/2017 | Matonick et al. | |
| 2020/0054796 A1 * | 2/2020 | Kaplan | A61L 31/022 |

\* cited by examiner

FULL-CIRCUMFERENTIAL TISSUE RESECTIONING

CROSS REFERENCE TO RELATED APPLICATIONS

This application claims the benefit of priority under 35 U.S.C. § 119 to U.S. Provisional Patent Application Ser. No. 62/670,015, filed on May 11, 2018, which is incorporated by reference in its entirety for all purposes.

FIELD

The present disclosure relates generally to resectioning devices and, more particularly, to endoscopic full circumferential resectioning devices for resectioning tissue in the gastrointestinal tract.

BACKGROUND

Resectioning procedures involve excising a portion of an organ, reconnecting the surrounding sections together to close up the hole created by the excision, and removing the excess tissue resulting from the stapling. Various conventional devices are available for resectioning lesions in tubular organs. Several known resectioning devices require at least one incision in an area near the portion of the organ to be excised because, for example, the resectioning device may lack steering and/or viewing capabilities. Specifically, devices for performing circular anastomoses of substantially tubular organs have been used in conjunction with open surgery. For example, devices are known for use in joining sections of the colon, which have been separated from one another by the surgical removal of a cylindrical section of the colon. The separated ends are first purse stringed to seal the interior of the colon, and a part of the device (e.g., the anvil of a stapling apparatus) is placed within one of the purse stringed ends, while the rest of the device is advanced through the colon to the other purse stringed end (usually via an additional incision). The two purse stringed ends are then brought together and the anvil is joined to the rest of the device. A circular line of staples joins the two sections of the colon and the tissue radially within this line of staples is cut away and removed to open the lumen of the rejoined colon. Of course, these incisions are painful and may involve a partial or entire loss of mobility while recuperating from the incision, in addition to the pain and inconvenience associated with recovery from the resectioning procedure itself. Furthermore, the time required to recover from such a procedure is often longer than for procedures which do not require incisions.

Deep invasive cancers, such as T1 and T2 lesions, cannot be resected using conventional minimally invasive endoscopic techniques today, such as endoscopic mucosal resectioning (EMR) and Endoscopic Submucosal Dissection (ESD), since they are only able to remove cancerous tissue no deeper than the submucosal layer. Intentional full thickness resectioning (FTR) is an alternative approach, but has a high risk profile. Challenges for FTR include post-operative leakage, and awareness of adjacent anatomy. With current techniques and devices, the endoscopic treatment of non-lifting lesions or deep submucosal or muscular invasion is difficult. When FTR is not an option to safely remove deeper-reaching cancers, laparoscopic surgery, which is more invasive and increases patient risk, is often the next approach.

SUMMARY

The present disclosure in its various embodiments relates generally to apparatus, devices, and methods for performing endoscopic full-circumferential resectioning of tissue in the lower gastrointestinal tract. In one or more embodiments of the present disclosure, a tissue resectioning device may include a first scaffold and a second scaffold, each of the first and second scaffolds having a substantially tubular configuration. The tissue resectioning device may further include a hook tool engaged with the first scaffold, the hook tool operable to bias the first scaffold and the second scaffold relative to one another to engage a section of tissue between the first scaffold and the second scaffold. In some embodiments, the first scaffold may include a first cutting surface, wherein the second scaffold includes a second cutting surface, and wherein the first cutting surface and the second cutting surface engage one another to resectioning the section of tissue. In some embodiments, the first cutting surface and the second cutting surface may matingly engage one another. In some embodiments, each of the first scaffold and the second scaffold may include a main body having an inner surface and an outer surface, wherein the inner surface circumscribes a central longitudinal axis, and a plurality of attachment tangs extending from the main body, wherein the plurality of attachment tangs is operable to engage an interior tissue wall. In some embodiments, the main body may include a plurality of slots extending around a circumference of the main body, and a locking tab at an end of the main body, wherein the locking tab extends through one of the plurality of slots to maintain the main body in a substantially tubular configuration. In some embodiments, the plurality of attachment tangs may bend radially away from the central longitudinal axis. In some embodiments, the second scaffold may include a set of endoscope tabs extending from the main body, wherein the set of endoscope tabs bend towards the central longitudinal axis. In some embodiments, a set of fasteners may couple together the first and second scaffolds. In some embodiments, the hook tool may extend through the first and second scaffolds. The hook tool may include a first plurality of hooks engaged with the first scaffold, and a second plurality of hooks engageable with the section of tissue. In some embodiments, the hook tool may include a set of spears engageable with the section of tissue. In some embodiments, the first scaffold may extend partially over the second scaffold when the section of tissue is engaged between the first scaffold and the second scaffold.

In one or more embodiments of the present disclosure, a tissue resectioning apparatus may include a scope and a tissue resectioning device around the scope. The tissue resectioning device may include a first scaffold and a second scaffold, each of the first and second scaffolds having a substantially tubular configuration. The tissue resectioning apparatus may further include a hook tool engaged with the first scaffold, the hook tool operable to bias the first scaffold relative to the second scaffold to engage a section of tissue between the first scaffold and the second scaffold. In one or more embodiments, the tissue resectioning apparatus may further include an overtube, wherein the scope and the tissue resectioning device extend within a lumen of the overtube. In one or more embodiments, the first scaffold may include a first cutting surface, wherein the second scaffold includes a second cutting surface, and wherein the first cutting surface and the second cutting surface engage one another to resectioning the section of tissue. In one or more embodiments, each of the first scaffold and the second scaffold may include a main body having an inner surface and an outer surface, the inner surface circumscribing a central longitudinal axis. The main body may include a plurality of slots extending around a circumference of the main body, and a locking tab at an end of the main body, wherein the locking tab extends through one of the plurality of slots to maintain the main body in a substantially tubular configuration. The main body may further include a plurality of attachment tangs extending radially from the main body and from the central longitudinal axis, the plurality of attachment tangs operable to engage an interior tissue wall.

In one or more embodiments of the present disclosure, a method for tissue resectioning may include inserting a tissue resectioning device into a gastrointestinal (GI) tract, the tissue resectioning device including a first scaffold and a second scaffold, each of the first and second scaffolds having a substantially tubular configuration. The tissue resectioning device may further include a hook tool engaged with at least one of the first scaffold and the second scaffold. The method may further include biasing, using the hook tool, the first scaffold and the second scaffold relative to one another to resection a target section of tissue of the GI tract captured between the first scaffold and the second scaffold. In some embodiments, the method may include positioning the first scaffold along a first side of the target section of tissue of the GI tract, and positioning the second scaffold along a second side of the target section of tissue of the GI tract. The first scaffold and second scaffold may be separated from one another by a gap. The method may further include engaging the first scaffold with the hook tool by inserting the hook tool through the first scaffold and the second scaffold, and moving the first scaffold towards the second scaffold using the hook tool to engage the target section of tissue of the GI tract between the first scaffold and the second scaffold. In some embodiments, the method may include engaging the section of tissue of the GI tract with a second plurality of hooks of the hook tool, and moving the target section of tissue of the GI tract inwards towards a central longitudinal axis of the tissue resectioning device, wherein the target section of tissue of the GI tract is brought into a path of a cutting surface of each of the first and second scaffolds. In some embodiments, the method may include securing the first and second scaffolds within the GI tract using a plurality of attachment tangs extending radially from the tissue resectioning device. In some embodiments, the method may further include biasing the first scaffold relative to the second scaffold until the first scaffold overlaps with the second scaffold, wherein a diameter of the first scaffold is different than a diameter of the second scaffold.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

Figure 1:
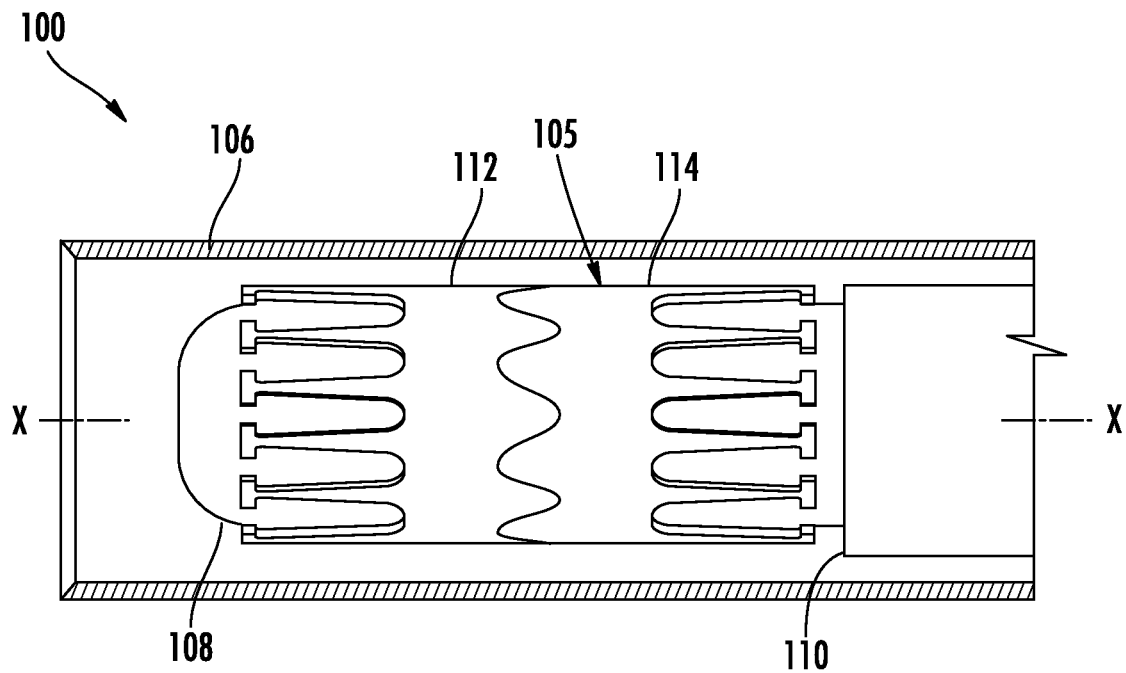
FIG. 1 is a side partial cross-sectional view of a full-circumferential tissue resectioning apparatus according to embodiments of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Embodiments herein disclose endoscopic tissue resectioning apparatuses, devices, and methods for minimally invasive tissue resectioning. Those skilled in the art will appreciate that while the devices and approaches of the present disclosure will herein be described with reference to full circumferential resectioning of the colon, the apparatuses, devices, and approaches may be utilized in other digestive tract transluminal procedures, and may be introduced transorally as well as transanally.

Embodiments herein disclose approaches for focally or full-circumferentially resection of tissue from the GI tract (e.g., lower or upper). These approaches enable physicians to perform tissue resections using minimally invasive methods rather than surgical methods. In some embodiments, a tissue resectioning device may include a first scaffold and a second scaffold, each of the first and second scaffolds having a substantially tubular configuration. A hook tool engages the first scaffold, and is operable to bias the first scaffold and the second scaffold relative to one another. The hook tool is further operable to engage a section of tissue between the first scaffold and the second scaffold. The first and second scaffolds may include cutting surfaces to engage and then resection the section of tissue. Although non-limiting, the cutting surfaces matingly engage one another in some embodiments.

In various embodiments, the first and second scaffolds each include a main body having an inner surface and an outer surface, the inner surface circumscribing a central longitudinal axis. A plurality of attachment tangs may extend from the main body for engagement with an interior tissue wall of the colon. In some embodiments, the attachment tangs bend radially away from the central longitudinal axis. In yet other embodiments, a set of endoscope tabs may extend from the main body. The set of endoscope tabs bends towards the central longitudinal axis for engagement with an endoscope.

To maintain the tubular shape of the first and second scaffolds, the main body may include a plurality of slots extending around a circumference of the main body, wherein a locking tab extends through one of the plurality of slots. Once the first and second scaffolds are brought together, a set of fasteners may physically/mechanically couple together the first and second scaffolds. For example, the set of fasteners extends through the plurality of slots when the first scaffold is coupled to the second scaffold. In some embodiments, each of the set of fasteners is a tab engageable with a perimeter wall of the plurality of slots.

In various embodiments, the hook tool extends through the first and second scaffolds, for example, substantially along the central longitudinal axis. The hook tool may include a first plurality of hooks engaged with the first scaffold, and a second plurality of hooks engageable with the section of tissue to be resectioned. The second plurality of hooks may resemble grapple hooks that grab the tissue to be removed, and push the tissue into an area between the first and second scaffolds as the first and second scaffolds are closed together. In some embodiments, the hook tool comprising a set of spears engageable with the section of tissue.

In various embodiments, a diameter of the first scaffold is the same as a diameter of the second scaffold. However, in other embodiments, a diameter of the first scaffold is different than a diameter of the second scaffold. As a result, the first scaffold may overlap or extend partially over the second scaffold when the section of tissue is engaged between the first scaffold and the second scaffold.

Figure 2:
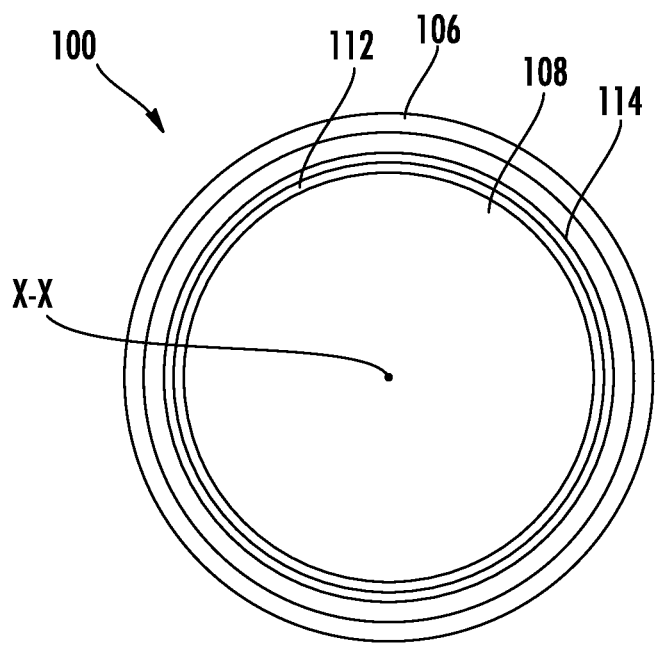
FIG. 2 is an end view of the full-circumferential tissue resectioning apparatus of FIG. 1 according to embodiments of the present disclosure.

Turning now to FIGS. 1-2, a full-circumferential tissue resectioning apparatus (hereinafter "apparatus") 100 according to embodiments of the disclosure will be described in greater detail. As shown, the apparatus 100 may include a full-circumferential tissue resectioning device (hereinafter "device") 105, which is deliverable endoscopically to a surgical site within the colon of patient via an overtube 106. The device 105 may be disposed around an endoscope 108, which is connected to a push tube 110. The device 105 is movable along a central longitudinal axis X-X of the overtube 106 by the endoscope 108 and the push tube 110.

As shown, the device 105 may include a first scaffold 112 and a second scaffold 114 extending along the endoscope 108. The first and second scaffolds 112, 114 may have a substantially tubular configuration. The device 105 is arranged concentrically around the central longitudinal axis x-x. In exemplary embodiments, when the device 105 is in a closed configuration, the first and second scaffolds 112, 114 abut one another, for example, as shown.

Figure 3:
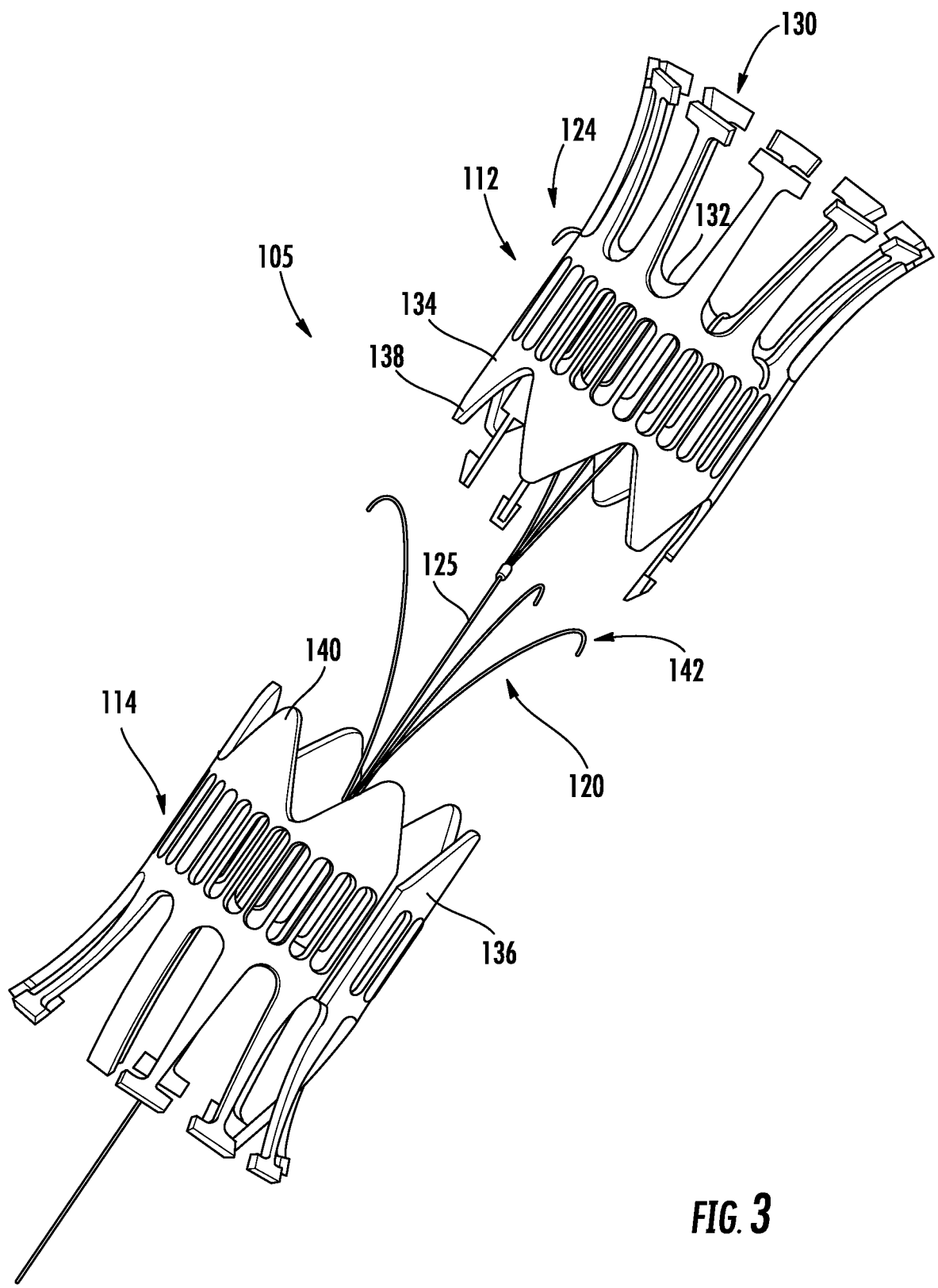
FIG. 3 is a perspective view of a full-circumferential tissue resectioning device in a first configuration according to embodiments of the present disclosure.
Figure 4:
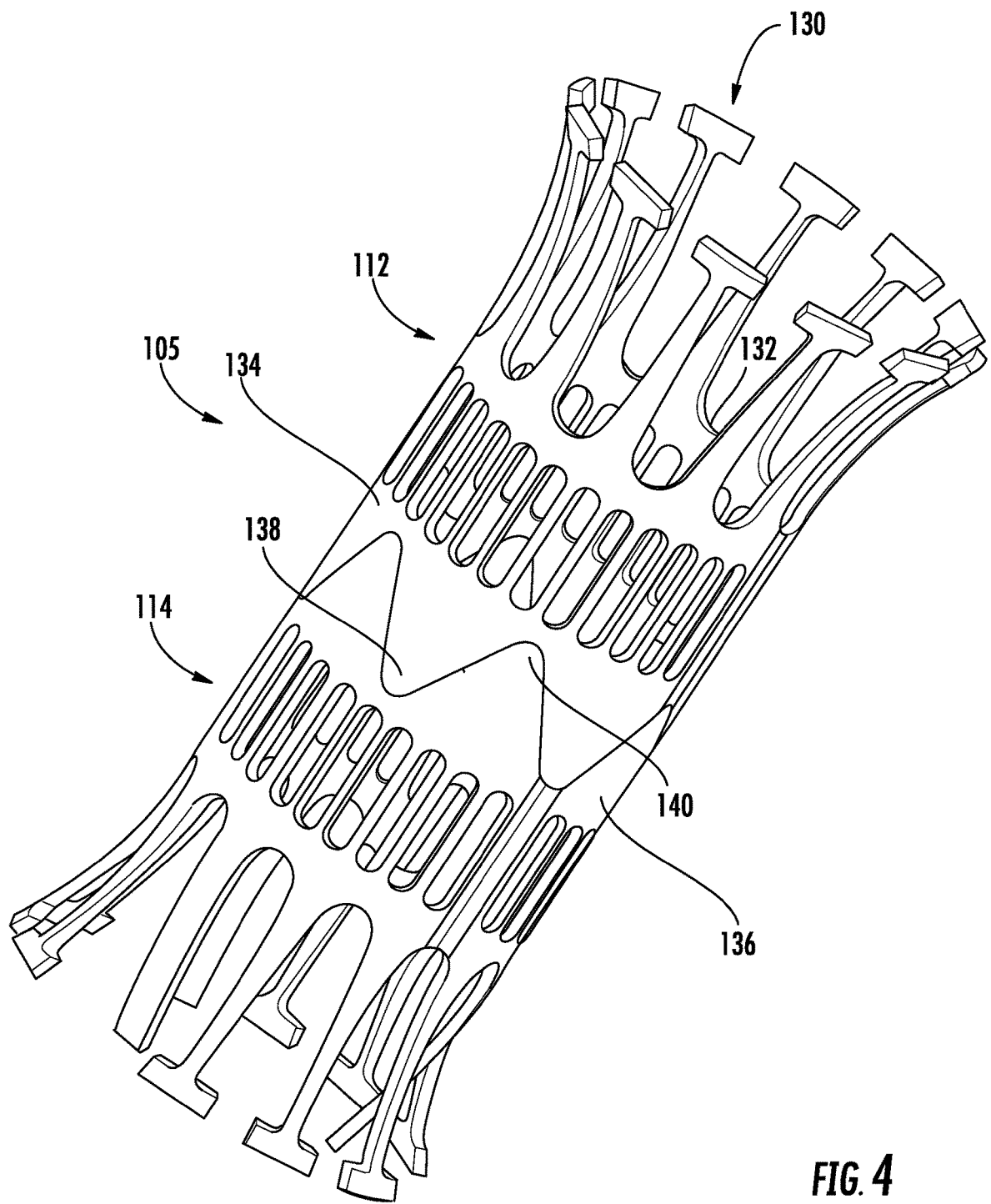
FIG. 4 is a perspective view of the full-circumferential tissue resectioning device of FIG. 3 in a second configuration according to embodiments of the present disclosure.

Turning now to FIGS. 3-4, the device 105 according to embodiments of the present disclosure will be described in greater detail. As shown, the device 105 may further include a hook tool 120 extending through a central cavity of the first scaffold 112 and the second scaffold 114. The hook tool 120 is operably engaged with the first scaffold 112 to bias the first scaffold 112 and/or the second scaffold relative one another. For example, as will be described in greater detail below, the hook tool 120 causes the first scaffold 112 to be moved from a first position, shown in FIG. 3, to a second position (FIG. 4), in which a target section of tissue (e.g., a cancerous portion of the colon) is engaged between the first scaffold 112 and the second scaffold 114. In other embodiments, the hook tool 120 may also be engaged with the second scaffold.

In some embodiments, the hook tool 120 includes a first plurality of hooks 124 extending from a base wire 125. The first plurality of hooks 124 may be engaged with the first scaffold 112, for example, between a plurality of attachment tangs 130. As shown, the first plurality of hooks 124 may extend around an outer edge 132 of a main body 134 of the first scaffold 112. In the non-limiting embodiment shown, the first plurality of hooks 124 may include three (3) hooks. In other embodiments, a fewer or greater number of hooks may be employed.

During use, as the hook tool 120 is brought towards the second scaffold 114, the first plurality of hooks 124 grab the main body 134 and bring it towards a main body 136 of the second scaffold 112. When the device 105 is closed, for example as shown in FIG. 4, the main body 134 of the first scaffold 112 matingly engages the main body 136 of the second scaffold 114 in an end-to-end fashion. The first scaffold 112 and the second scaffold 114 may have a same, or substantially the same, diameter. In some embodiments, the main body 134 of the first scaffold 112 and the main body 136 of the second scaffold 114 each have complementary surface features 138 and 140, which are offset circumferentially from one another so as to form a continuous or substantially continuous, tubular structure.

As further shown in FIG. 3, the hook tool 120 may include a second plurality of hooks 142 extending from the base wire 125. When the device 105 is in the open position, the second plurality of hooks 142 is generally positioned between the first scaffold 112 and the second scaffold 114. The second plurality of hooks 142 is configured to grab the target section of tissue to be removed, and pull the target section of tissue into the device 105 as the first scaffold 112 is pulled towards the second scaffold 114 and closed. In the non-limiting embodiment shown, the second plurality of hooks 142 may include three (3) hooks. In other embodiments, a fewer or greater number of hooks may be employed.

Figure 5:
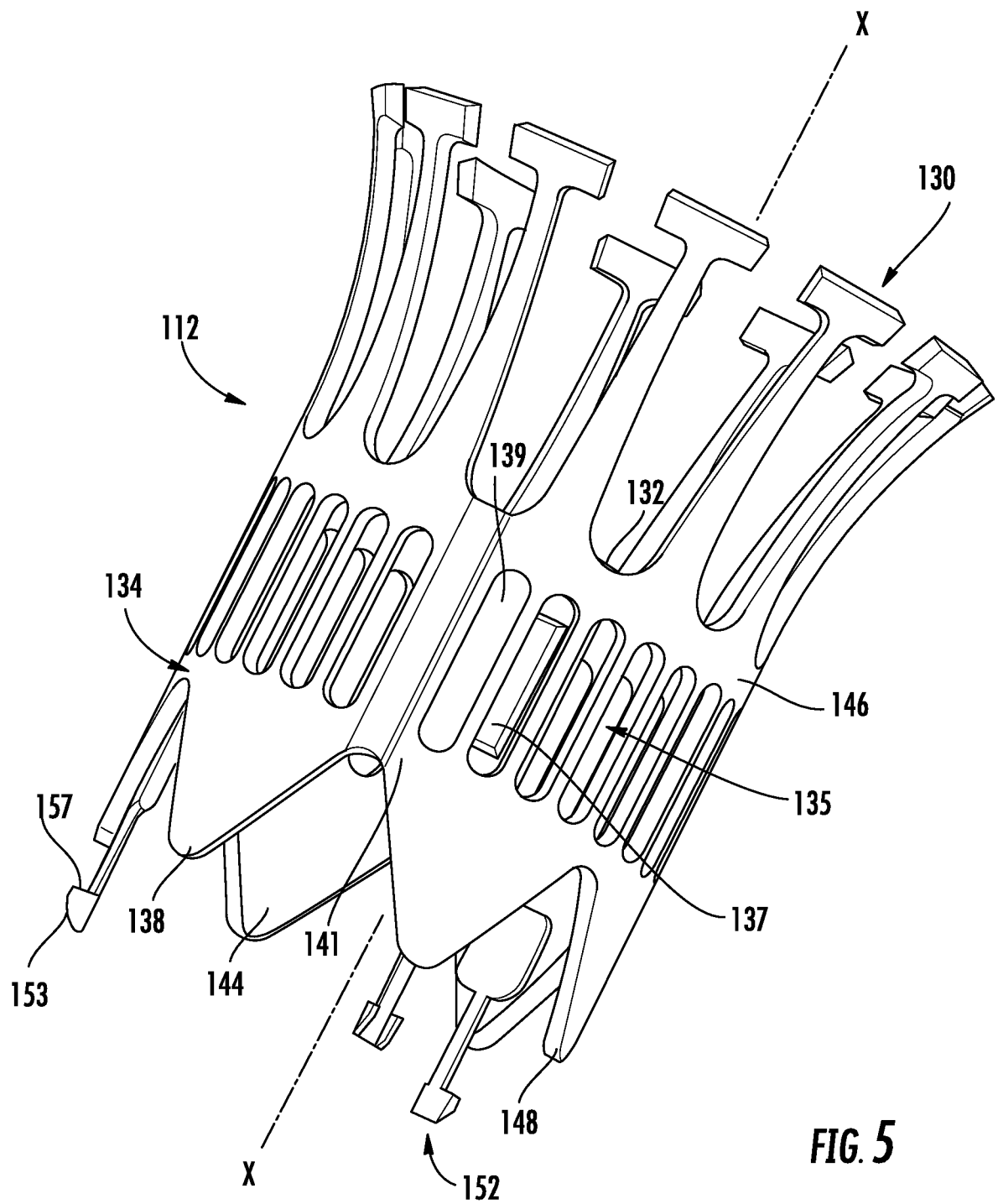
FIG. 5 is a perspective view of a first scaffold of the full-circumferential tissue resectioning device of FIG. 3 according to embodiments of the present disclosure.

Turning now to FIG. 5, the first scaffold 112 according to embodiments of the present disclosure will be described in greater detail. As shown, the first scaffold 112 may include the main body 134 having an inner surface 144 and an outer surface 146. The inner surface 144 may be disposed concentrically, or substantially concentrically, around the central longitudinal axis x-x. The first scaffold 112 may include the outer edge 132 opposite an inner edge 148 along an axial or lengthwise direction. The inner edge 148 may be a cutting surface, wherein the surface features 138 are serrations or "teeth" operable to cut through the target section of tissue.

Extending from the outer edge 132 of the main body 134 are the plurality of attachment tangs 130. In the non-limiting embodiment shown, each of the plurality of attachment tangs 130 bends radially away from the central longitudinal axis x-x to affix the first scaffold 112 to the inner wall of the colon. In various embodiments, the plurality of attachment tangs 130 may be integrally formed with the main body 134, or may be separate components coupled thereto.

As further shown, the first scaffold 112 may include a plurality of slots 135 extending around a circumference of the main body 134. In the non-limiting embodiment shown, each of the plurality of slots 135 extends completely through the main body 134. A locking tab 137 may be provided at a first end 139 of the main body 134. As shown, the locking tab 137 may be positioned within one of the plurality of slots 135 to prevent the main body 134 from contracting. Said differently, the locking tab 137 maintains the main body 134 in a substantially tubular, expanded configuration. In the non-limiting embodiment shown, the first end 139 of the main body 134 may be a free end, which may be circumferentially overlapped by a second end 141.

Figure 6:
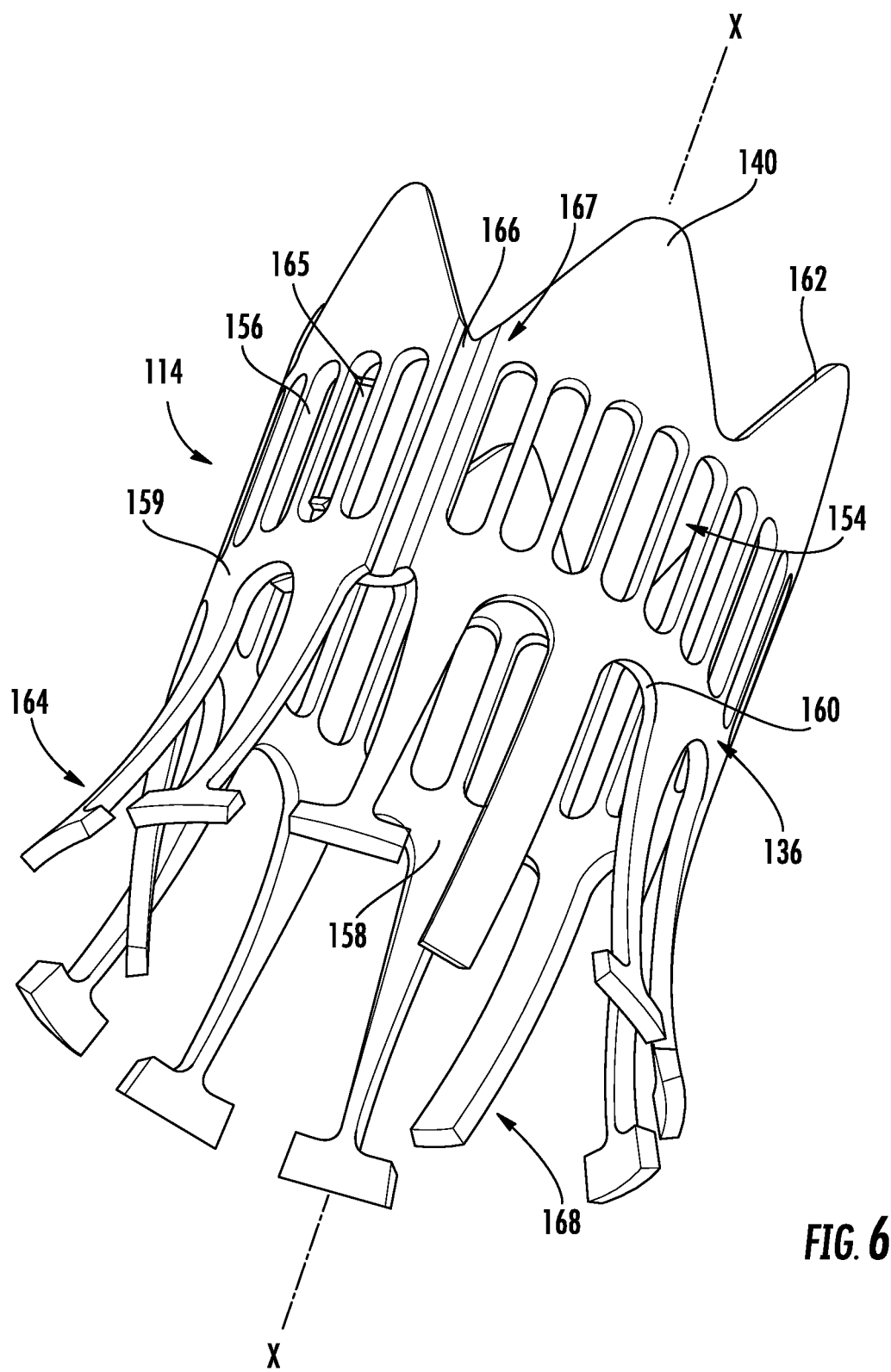
FIG. 6 is a perspective view of a second scaffold of the full-circumferential tissue resectioning device of FIG. 3 according to embodiments of the present disclosure.

With reference to FIGS. 5-6, the first scaffold 112 may include a set of fasteners 152 for coupling together the main body 134 of the first scaffold 112 with the main body 136 of the second scaffold 114. In the non-limiting embodiment shown, the set of fasteners 152 may extend through a plurality of slots 154 of the main body 136 of the second scaffold 114 when the first scaffold 112 is joined to the second scaffold 114. More specifically, each of the set of fasteners 152 may include a tab 153 engageable with a perimeter wall 156 defining each of the plurality of slots 154. The tab 153 includes an engagement surface 157 facing the perimeter wall 156. After the tabs 153 move into the plurality of slots 154, the engagement surface 157 in abutment with the perimeter wall 156 to prevent the first scaffold 112 and the second scaffold 114 from becoming disengaged from one another.

Referring to FIG. 6, the second scaffold 114 may include the main body 136 having an inner surface 158 and an outer surface 159. The inner surface 158 may be disposed concentrically, or substantially concentrically, around the central longitudinal axis x-x. The second scaffold 114 may include an outer edge 160 opposite an inner edge 162 along an axial or lengthwise direction. The inner edge 162 may be a cutting surface, wherein the surface features 140 are serrations or "teeth" operable to cut through the target section of tissue. In exemplary embodiments, the surface features 138 of the first scaffold 112 and the surface features 140 of the second scaffold engage one another to resection the target section of tissue.

Extending from the outer edge 160 of the main body 136 are a second plurality of attachment tangs 164. In the non-limiting embodiment shown, each of the second plurality of attachment tangs 164 bend or extend radially away from the central longitudinal axis x-x to affix the second scaffold 114 to the inner wall of the colon. The second plurality of attachment tangs 164 may be integrally formed with the main body 136, or may be separate components coupled thereto.

As further shown, the second scaffold 114 may include the plurality of slots 154 extending around a circumference of the main body 136. In the non-limiting embodiment shown, each of the plurality of slots 154 extends completely through the main body 136. A locking tab 165 is provided at a first end 166 of the main body 136. The locking tab 165 may be positioned within one of the plurality of slots 154 to prevent the main body 136 from contracting. Said differently, the locking tab 165 maintains the main body 136 in a substantially tubular, expanded configuration. In the non-limiting embodiment shown, the first end 166 of the main body 136 may be a free end, which may be circumferentially overlapped axially by a second end 167.

In various embodiments, the second scaffold 114 may include a set (i.e., one or more) endoscope tabs 168 extending from the outer edge 160 of the main body 136. As shown, the set of endoscope tabs 168 bend radially towards the central longitudinal axis x-x for engagement with the endoscope 108 (FIG. 1). In some embodiments, the set of endoscope tabs 168 bear against the endoscope 108 to prevent the first and second scaffolds 112, 114 from moving in tandem towards the endoscope 108. In various embodiments, the set of endoscope tabs 168 may be integrally formed with the main body 136, or may be separate components coupled thereto. In the non-limiting embodiment shown, the set of endoscope tabs 168 may include three (3) tabs. In other embodiments, a fewer or greater number of tabs may be employed.

Figure 7A:
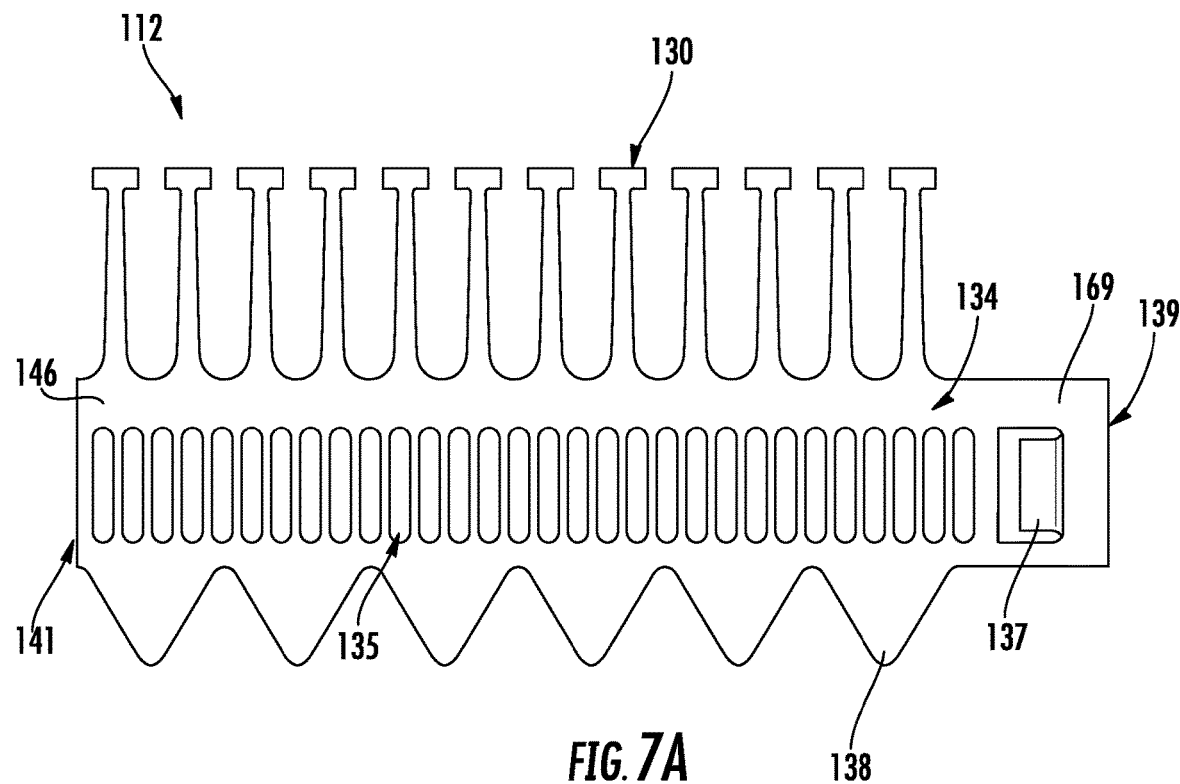
FIG. 7A is a top view of the first scaffold of the full-circumferential tissue resectioning device of FIG. 3 according to embodiments of the present disclosure.
Figure 7B:
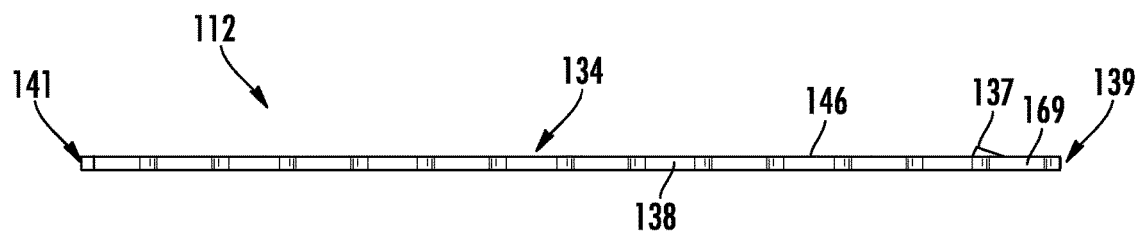
FIG. 7B is a side view of the first scaffold of the full-circumferential tissue resectioning device of FIG. 3 according to embodiments of the present disclosure.

Turning now to FIGS. 7A-7B, the first scaffold 112 according to embodiments of the present disclosure will be described in greater detail. Although only the first scaffold 112 is shown, it will be appreciated that the second scaffold 114 may be similarly configured. In this embodiment, the first scaffold 112 may starts as a flat, stamped piece of sheet metal, such as stainless steel, titanium, or nitinol. Each of the features of the first scaffold 112, including the plurality of attachment tangs 130, the plurality of slots 135, the surface features 138, and the locking tab 137 may then be formed using a die stamping or die pressing process.

For example, in various embodiments, the first scaffold 112 may be formed by placing flat sheet metal in either blank or coil form into a stamping press where a tool and die surface forms the metal into a net shape. Stamping includes a variety of sheet-metal forming manufacturing processes, such as punching using a machine press or stamping press, blanking, embossing, bending, flanging, and coining. This could be a single stage operation where every stroke of the press produces the desired form on coupling, or could occur through a series of stages. The process may be carried out on sheet metal, but can also be used on other materials, such as polystyrene. In some embodiments, stamping may be done on cold metal sheet.

As shown, the first end 139 of the main body 134 may be a free end tab 169. In the non-limiting embodiment shown, the locking tab 137 is formed from the free end tab 169. The locking tab 137 is configured to extend above a plane defined by the outer surface 146 of the first scaffold 112. The first scaffold 112 may be rolled to a tight coil, for over-the-scope delivery. When the first scaffold 112 is arranged in a tubular configuration, the second end 141 overlaps the free end tab 169 to position the locking tab 137 within one of the plurality of slots 135.

Figure 8:
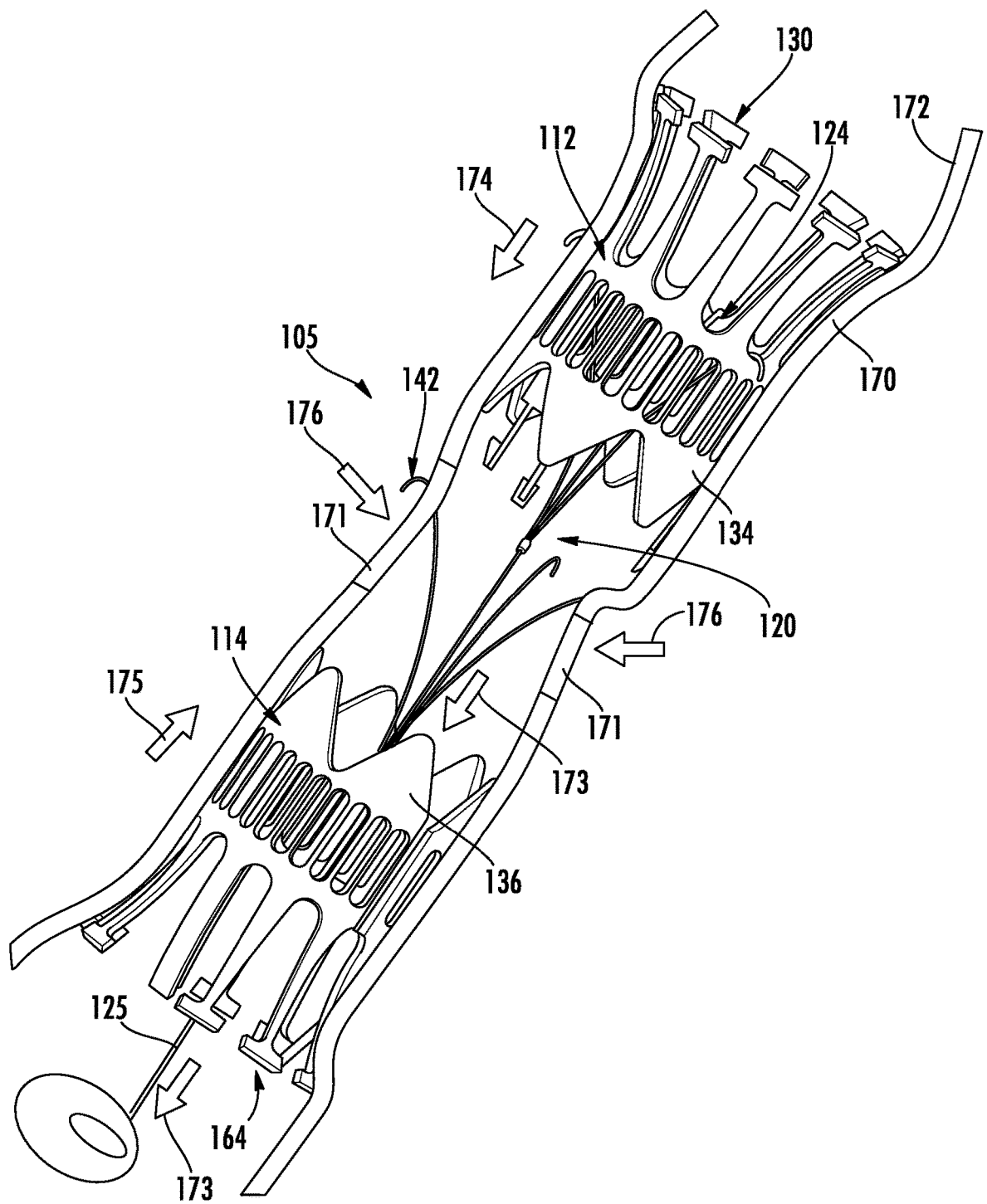
FIGS. 8-9 are perspective views of the full-circumferential tissue resectioning device of FIG. 3 within a colon of a patient according to embodiments of the present disclosure.
Figure 9:
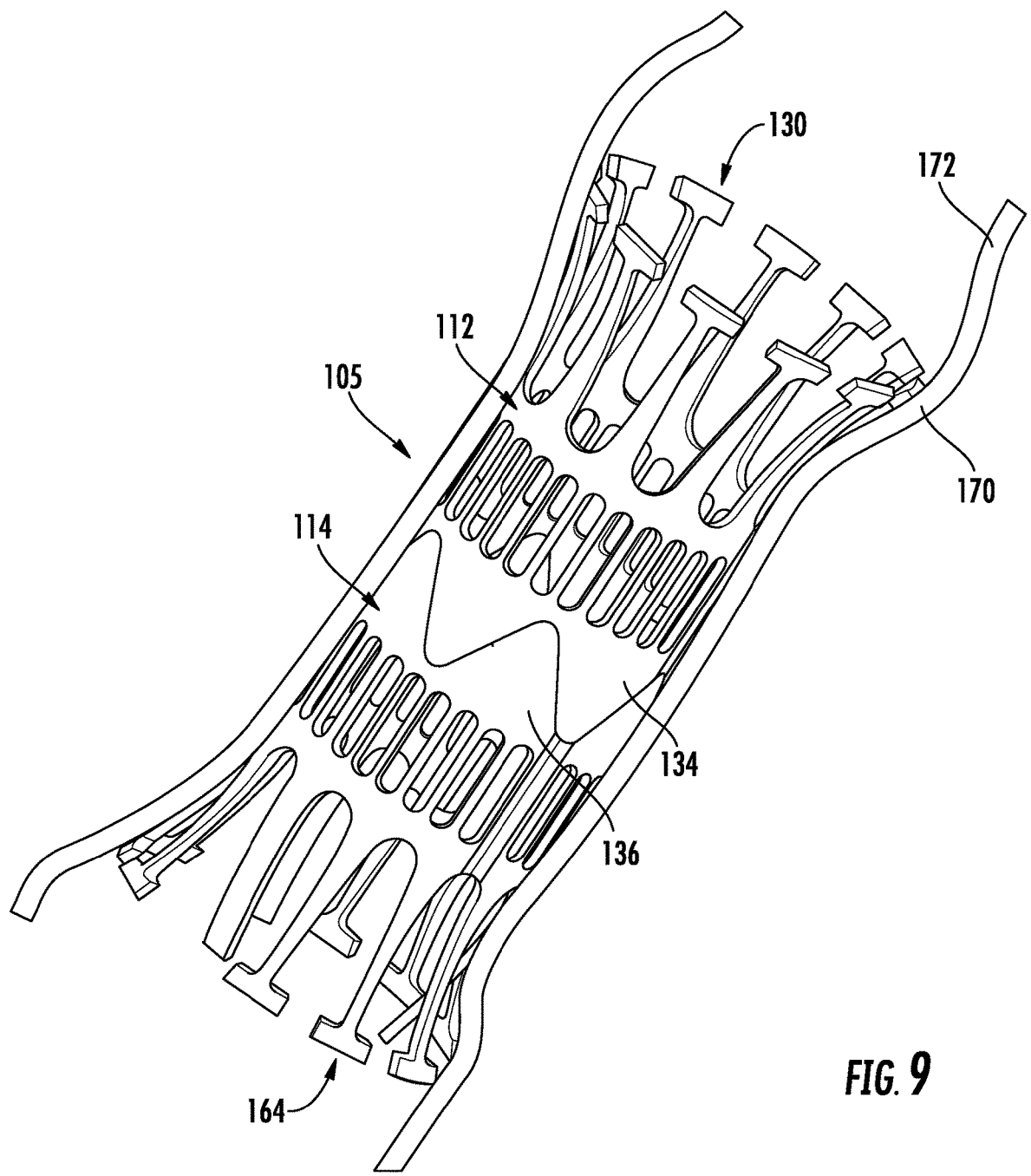

Turning now to FIGS. 8-9, operation of the device 105 within a colon 170 of a patient according to embodiments of the present disclosure will be described in greater detail. As shown in FIG. 8, the device 105 may be delivered by the endoscope to a desired position within the colon 170. In some embodiments, the first scaffold 112 is inserted rectally in a delivery system such as the overtube 106 shown in FIGS. 1-2. The first scaffold 112 is inserted into the colon 170 above a target section of tissue 171. Using a balloon (e.g. CRE Balloon Dilator), the first scaffold 112 may be expanded until the diameter of the main body 134 of the first scaffold 112 matches the diameter of the colon 170. Delivery and observation of the first scaffold 112 may be done under fluoroscopic or endoscopic guidance. The first plurality of attachment tangs 130 of the first scaffold 112 may then be affixed to an interior wall 172 of the colon 170.

The second scaffold 114 is then similarly inserted into the colon 170 below the target section of tissue 171. Using the balloon, the second scaffold 114 may be expanded until the diameter of the main body 136 of the second scaffold 114 matches the diameter of the colon 170 and the diameter of the first scaffold 112. The second plurality of attachment tangs 164 of the second scaffold 114 may then be affixed to the interior wall 172 of the colon 170. At this stage, the first and second scaffolds 112, 114 are separated from one another, e.g., radially along the longitudinal axis, by a gap.

After the first and second scaffolds 112, 114 are attached into position, the hook tool 120 is brought into use. As shown, the first plurality of hooks 124 is attached with the first scaffold 112, for example, between a plurality of attachment tangs 130. The second plurality of hooks 142 is then inserted into the colon 170, e.g., in an area proximate the target section of tissue 171. The base wire 125 is then pulled towards the second scaffold 114, in a direction indicated by arrows 173, to draw the first scaffold 112 and the second scaffold 114 towards one another, as indicated by opposing directional arrows 174, 175. Movement of the base wire 125 further causes the second plurality of hooks 142 to be drawn towards the base wire 125 and towards the second scaffold 114, as indicated by directional arrows 176. The second plurality of hooks 142 bring the target section of tissue 171 into the path of the cutting surfaces of the first and second scaffolds 112, 114. When the first and second scaffolds 112, 114 are fully closed, as shown in FIG. 9, the target section of tissue 171 is resectioned. The excised target section of tissue 171 may then be removed, followed by the hook tool 120. At some point in the future, for example, days or weeks later, the device 105 may be removed from the colon 170.

Figure 10:
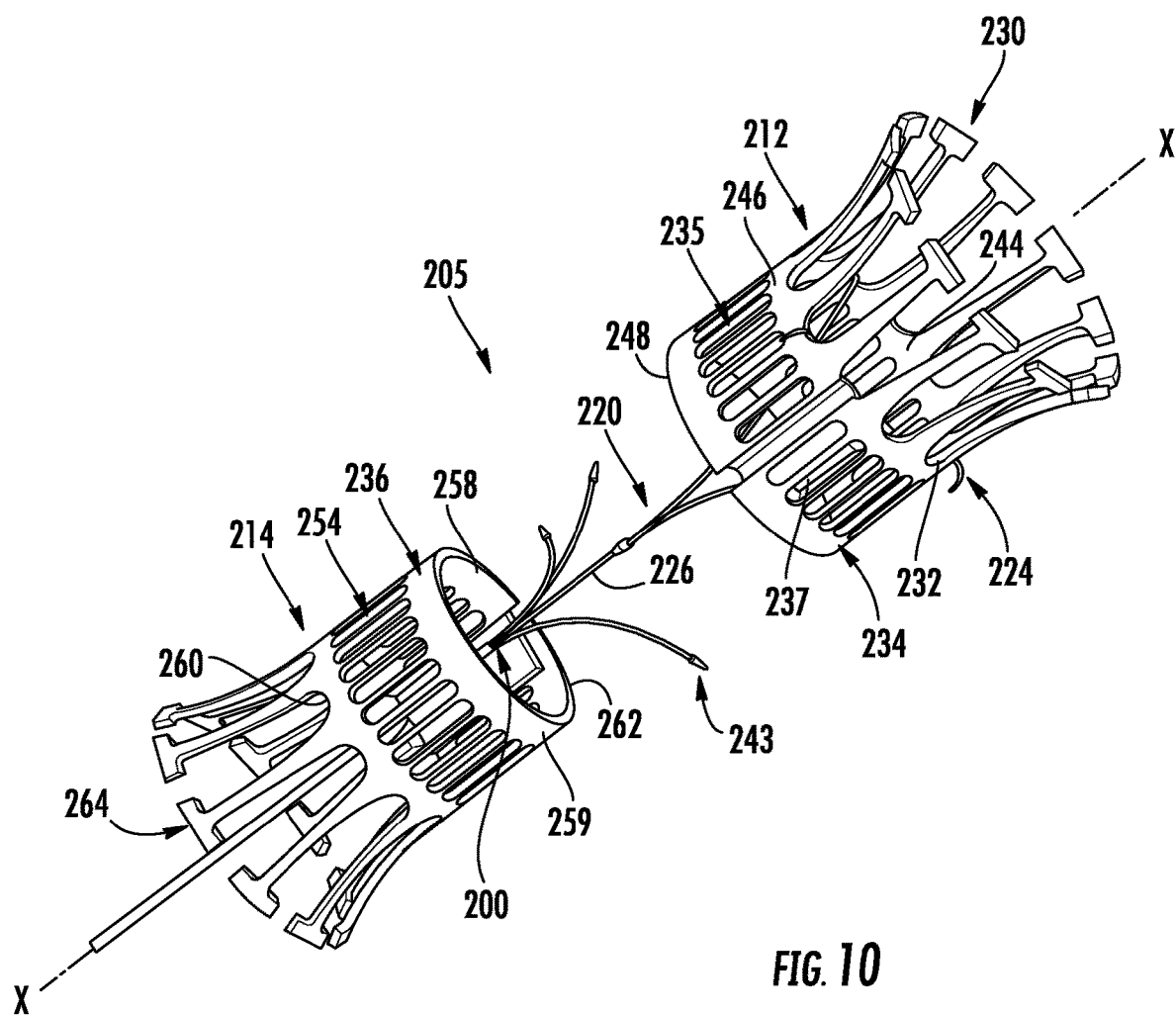
FIG. 10 is a perspective view of another full-circumferential tissue resectioning device in a first configuration according to embodiments of the present disclosure.
Figure 11:
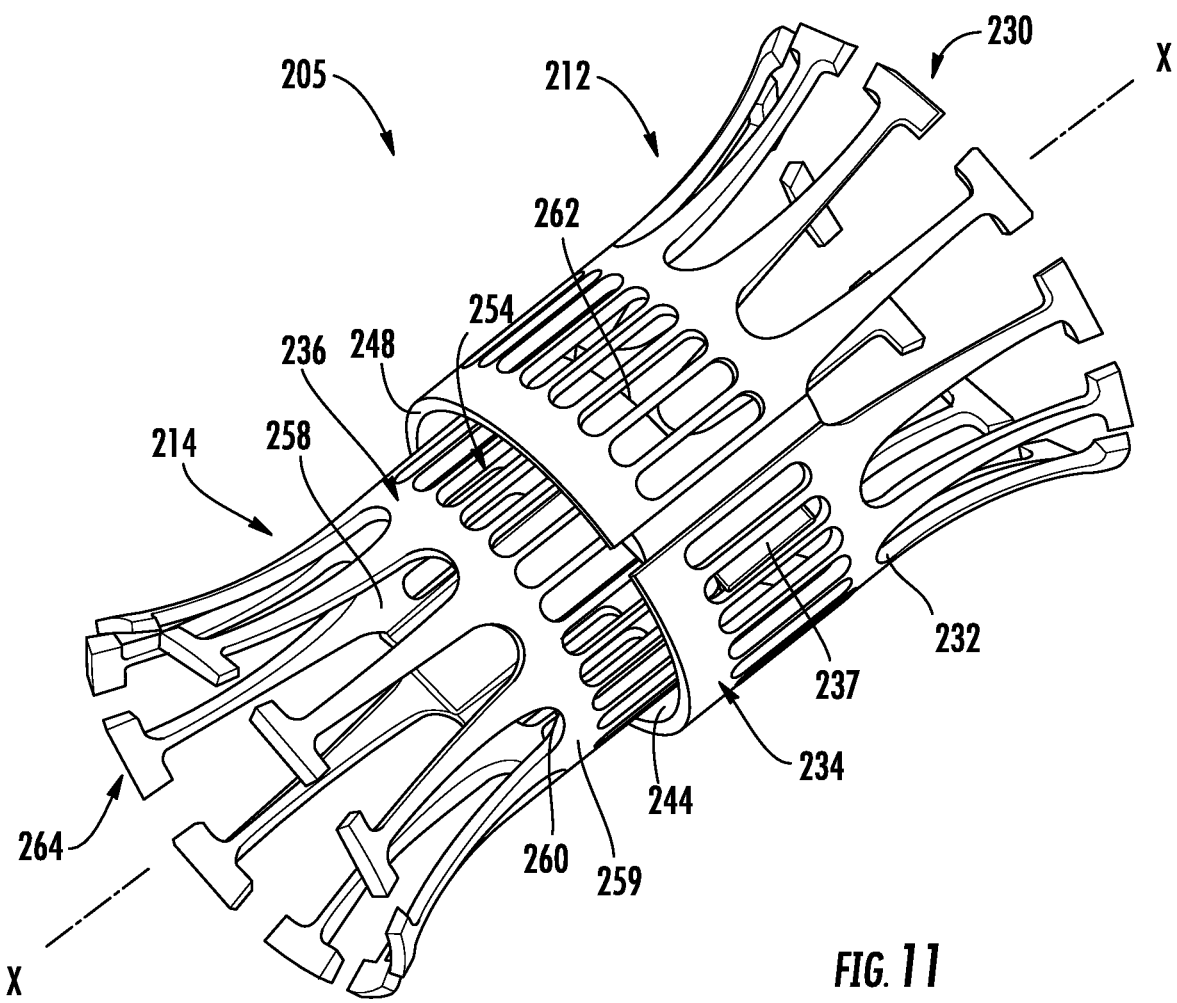
FIG. 11 is a perspective view of the full-circumferential tissue resectioning device of FIG. 10 in a second configuration according to embodiments of the present disclosure.

Turning now to FIGS. 10-11, another full-circumferential tissue resectioning device (hereinafter "device") 205 according to embodiments of the present disclosure will be described in greater detail. Although not shown, the device 205 may be deliverable endoscopically to a surgical site within the colon of patient via an overtube, such as the overtube 106 shown in FIGS. 1-2.

The device 205 may include a first scaffold 212 and a second scaffold 214 each arranged into a substantially tubular configuration. The first scaffold 212 and a second scaffold 214 may be arranged concentrically around a central longitudinal axis x-x. In exemplary embodiments, when the device 205 is in a closed configuration, such as the configuration shown in FIG. 11, the first scaffold 212 extends radially over the second scaffold 214. In order to do so, a diameter of the first scaffold 212 is different (e.g., larger) than a diameter of the second scaffold 214.

As shown, the device 205 may further include a hook tool 220 extending through a central cavity of the first scaffold 212 and the second scaffold 214. The hook tool 220 is operably engaged with the first scaffold 212 to bias the first scaffold 212 and the second scaffold 214 relative to one another. For example, as will be described in greater detail below, the hook tool 220 causes the first scaffold 212 to be moved from a first position, shown in FIG. 10, into a second position, shown in FIG. 11, in which a target section of tissue (e.g., a cancerous portion of the colon) is engaged between the first scaffold 212 and the second scaffold 214.

In some embodiments, the hook tool 220 includes a first plurality of hooks 224 extending from a base shaft 226. The first plurality of hooks 224 may engage the first scaffold 212, for example, between a plurality of attachment tangs 230. As shown, the first plurality of hooks 224 may extend around an outer edge 232 of a main body 234 of the first scaffold 212. In the non-limiting embodiment shown, the first plurality of hooks 224 may include three (3) hooks. In other embodiments, a fewer or greater number of hooks may be employed. During use, as the hook tool 220 is brought towards the second scaffold 214, the first plurality of hooks 224 grab the main body 234 and bring it towards a main body 236 of the second scaffold 212.

As further shown, the hook tool 220 may include a set of spears 243 extending from the base shaft 226 for engagement with an interior wall of the colon. In other embodiments, the hook tool 200 may include a second plurality of hooks to engage the colon. When the device 205 is in the open position shown in FIG. 10, the set of spears 243 is positioned generally between the first scaffold 212 and the second scaffold 214. The set of spears 243 is configured to grab the target section of tissue to be removed, and to push the target section of tissue into the device 205 as the first scaffold 212 is pulled towards the second scaffold 214 and closed. In the non-limiting embodiment shown, the set of spears 243 may include three (3) spears. In other embodiments, a fewer or greater number of spears may be employed.

In various embodiments, the first scaffold 212 may include the main body 234 having an inner surface 244 and an outer surface 246. The inner surface 244 may be disposed concentrically, or substantially concentrically, around the central longitudinal axis x-x. The first scaffold 212 may include the outer edge 232, and an inner edge 248 opposite the outer edge 232 along an axial or lengthwise direction. In this embodiment, the inner edge 248 may not include a cutting surface. Alternatively, the inner edge 248 can be used as a cutting guide, e.g., by allowing a blade to slide along the metal edge all around its circumference. The outer edge 232 may prevent the blade from extending too far, which can result in rupture of the tissue wall.

Extending from the outer edge 232 of the main body 234 are the plurality of attachment tangs 230. In the non-limiting embodiment shown, each of the plurality of attachment tangs 230 bends radially away from the central longitudinal axis x-x to affix the first scaffold 212 to the inner wall of the colon. In various embodiments, the plurality of attachment tangs 230 may be integrally formed with the main body 234, or may be separate components coupled thereto.

As further shown, the first scaffold 212 may include a plurality of slots 235 extending around a circumference of the main body 234. In the non-limiting embodiment shown, each of the plurality of slots 235 extends completely through the main body 234. A locking tab 237 is provided at one end of the main body 234. The locking tab 237 may be positioned within one of the plurality of slots 235 to prevent the main body 234 from contracting. Said differently, the locking tab 237 maintains the main body 234 in a substantially tubular, expanded configuration.

The second scaffold 214 may include the main body 236 having an inner surface 258 and an outer surface 259. The inner surface 258 may be disposed concentrically, or substantially concentrically, around the central longitudinal axis x-x. The second scaffold 214 may include an outer edge 260, and an inner edge 262 opposite the outer edge 260 along an axial or lengthwise direction. In the non-limiting embodiment shown in FIG. 11, the inner edge 262 of the second scaffold 214 may extend partially into the central cavity of the first scaffold 212 when the device 205 is in a closed configuration.

As further shown in FIGS. 10-11, extending from the outer edge 260 of the main body 236 of the second scaffold 214 is a second plurality of attachment tangs 264. In the non-limiting embodiment shown, each of the second plurality of attachment tangs 264 bend or extend radially away from the central longitudinal axis x-x to affix the second scaffold 214 to the inner wall of the colon. The second plurality of attachment tangs 264 may be integrally formed with the main body 236, or may be separate components coupled thereto.

The second scaffold 214 may further include the plurality of slots 254 extending around a circumference of the main body 236. In the non-limiting embodiment shown, each of the plurality of slots 254 extends completely through the main body 236. A locking tab may be positioned within one of the plurality of slots 254 to prevent the main body 236 from contracting. Said differently, the locking tab maintains the main body 236 in a substantially tubular, expanded configuration.

Figure 12A:
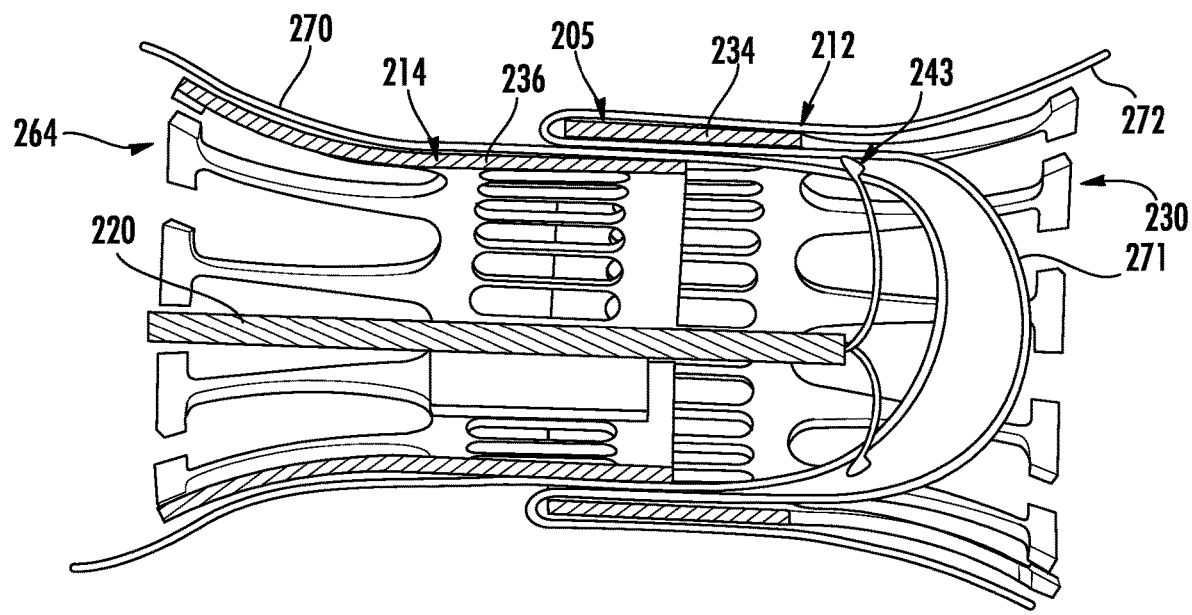
FIGS. 12A-12B are perspective views of the full-circumferential tissue resectioning device of FIGS. 10-11 within a colon of a patient according to embodiments of the present disclosure.
Figure 12B:
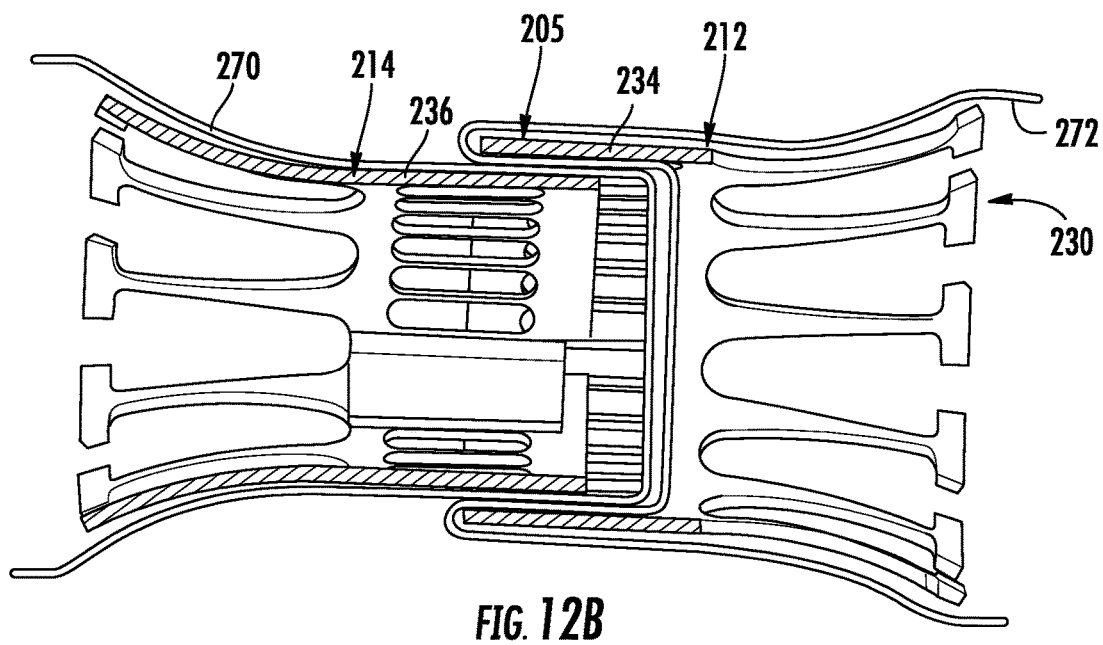

Turning now to FIGS. 12A-12B, operation of the device 205 within a colon 270 of a patient according to embodiments of the present disclosure will be described in greater detail. The device 205 may be delivered by an endoscope to a desired position within the colon 270, for example, above a target section of tissue. In some embodiments, the first scaffold 212 is inserted rectally in a delivery system such as the overtube 106 shown in FIGS. 1-2. Using a balloon (e.g. CRE Balloon Dilator), the first scaffold 212 may be expanded until the diameter of the main body 234 of the first scaffold 212 matches the diameter of the colon 270. Delivery and observation of the first scaffold 212 may be done under fluoroscopic or endoscopic guidance. The first plurality of attachment tangs 230 of the first scaffold 212 may then be affixed to an interior wall 272 of the colon 270.

The second scaffold 214 is then similarly inserted into the colon 270 to a position below the target section of tissue. Using the balloon, the second scaffold 214 may be expanded until the diameter of the main body 236 of the second scaffold 214 is slightly smaller than the diameter of the first scaffold 212. The first and second scaffolds 212, 214 may then be pulled together by the first plurality of hooks 224 (shown in FIGS. 10-11). The second plurality of attachment tangs 264 of the second scaffold 214 may then be affixed to the interior wall 272 of the colon 270. In this embodiment, reinsertion of the balloon to expand the second scaffold 214 seals the tissue between the first and second scaffolds 212, 214. The pressure advantageously provides a leak-proof seal, and staunches any bleeding.

After the first and second scaffolds 212, 214 are arranged into position, the hook tool 220 is brought into use. As shown, the set of spears 243 extending from the base shaft 226 engage the colon 270 and push a target section of tissue 271 into the central cavity of the first scaffold 212. In some embodiments, the base shaft 226 is rigid or substantially rigid. When the first and second scaffolds 212, 214 are fully closed, the target section of tissue 271 is resectioned. The excised target section of tissue 271 may then be removed, followed by the hook tool 220. In various embodiments, the target section of tissue 271 is removed using available cutting, cautery and removal tools.

Figure 13:
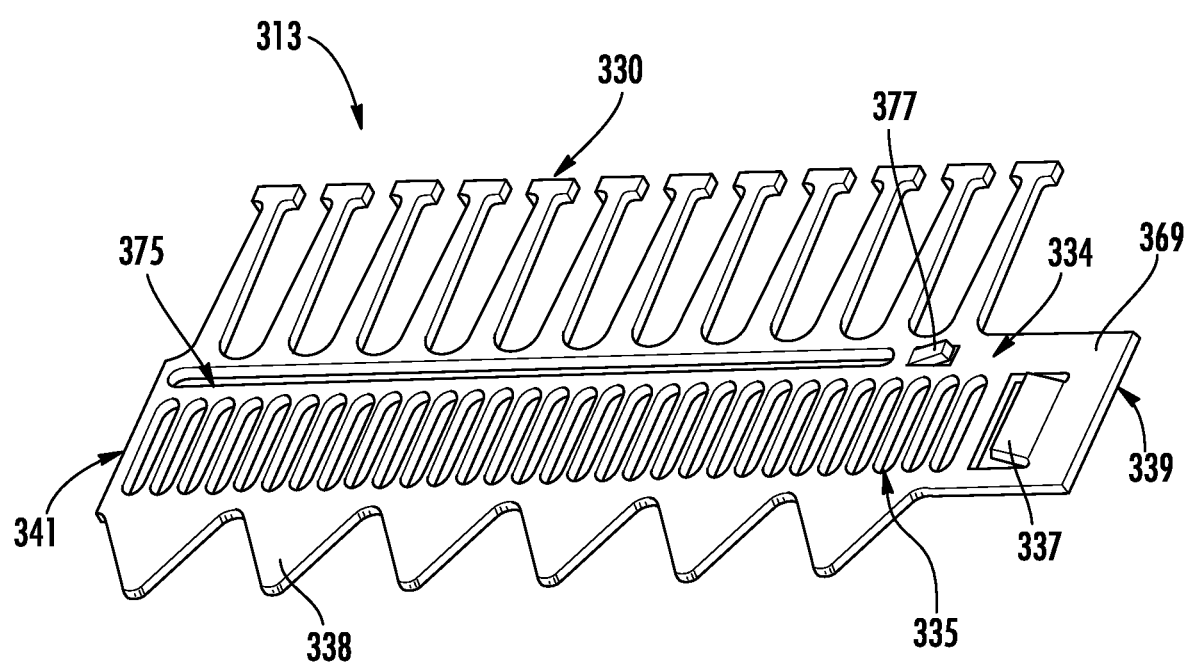
FIG. 13 is a perspective view of another scaffold according to embodiments of the present disclosure.

Turning now to FIG. 13, an alternative scaffold according to embodiments of the present disclosure will be described in greater detail. The scaffold 313 may represent any of the first and second scaffolds described above. As shown, the scaffold 313 may include a plurality of attachment tangs 330, the plurality of slots 335, the surface features 338, and the locking tab 337. The scaffold 313 may further include a free end tab 369 provided at a first end 339 of a main body 334. The scaffold 313 may be rolled to a tight coil, for over-the-scope delivery. When the scaffold 313 is arranged in a tubular configuration, a second end 341 overlaps the free end tab 369 to position the locking tab 337 within one of the plurality of slots 335.

In this embodiment, the scaffold 313 includes a circumferential slot 375 and sliding tab 377. When the scaffold 313 is arranged in the tubular configuration, the sliding tab 377 is positioned within the circumferential slot 375. The sliding tab 377 and the circumferential slot 375 ensure that any twisting of the scaffold 313 is less likely to disengage the locking tab 337 from the plurality of slots 335.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A tissue resectioning device, comprising:
   a first scaffold and a second scaffold, each of the first and second scaffolds having a substantially tubular configuration and annular cutting surfaces that oppose each other; and
   a hook tool comprising a first plurality of hooks and a second plurality of hooks, the hook tool engaged with the first scaffold, the first plurality of hooks of the hook tool operable to bias the first scaffold and the second scaffold relative to one another, and the second plurality of hooks of the hook tool operable to pull a section of tissue toward a central longitudinal axis of the device within a path of the annular cutting surfaces of the first and second scaffolds to engage the section of tissue between the first scaffold and the second scaffold.

2. The tissue resectioning device of claim 1, wherein the annular cutting surfaces of each of the first and second scaffolds are configured to engage one another to resect the section of tissue.

3. The tissue resectioning device of claim 2, wherein the annular cutting surfaces of each of the first and second scaffolds are configured to matingly engage one another.

4. The tissue resectioning device of claim 1, each of the first scaffold and the second scaffold comprising:
   a main body having an inner surface and an outer surface, the inner surface circumscribing the central longitudinal axis; and
   a plurality of attachment tangs extending from the main body, the plurality of attachment tangs operable to engage an interior wall of the section of tissue.

5. The tissue resectioning device of claim 4, the main body comprising:
   a plurality of slots extending around a circumference of the main body; and
   a locking tab at an end of the main body, the locking tab extending through one of the plurality of slots to maintain the main body in a substantially tubular configuration.

6. The tissue resectioning device of claim 5, the plurality of attachment tangs bending radially away from the central longitudinal axis.

7. The tissue resectioning device of claim 4, the second scaffold comprising a set of endoscope tabs extending from the main body, wherein the set of endoscope tabs bend towards the central longitudinal axis.

8. The tissue resectioning device of claim 4, further comprising a set of fasteners for coupling together the first and second scaffolds.

9. The tissue resectioning device of claim 1, wherein the hook tool is extendable through the first and second scaffolds.

10. The tissue resectioning device of claim 1, the hook tool comprising a set of spears engageable with the section of tissue.

11. The tissue resectioning device of claim 1, wherein the first scaffold extends partially over the second scaffold when the section of tissue is engaged between the first scaffold and the second scaffold.

12. A tissue resectioning apparatus comprising:
   a scope; and
   a tissue resectioning device around the scope, the tissue resectioning device comprising:
      a first scaffold and a second scaffold, each of the first and second scaffolds having a substantially tubular configuration and annular cutting surfaces that oppose each other; and
      a hook tool comprising a first plurality of hooks and a second plurality of hooks, the hook tool engaged with the first scaffold, the first plurality of hooks of the hook tool operable to bias the first scaffold relative to the second scaffold, and the second plurality of hooks of the hook tool operable to pull a section of tissue toward a central longitudinal axis of the device within a path of the annular cutting surfaces of the first and second scaffolds to engage the section of tissue between the first scaffold and the second scaffold.

13. The tissue resectioning apparatus of claim 12, further comprising an overtube, wherein the scope and the tissue resectioning device extend within a lumen of the overtube.

14. The tissue resectioning apparatus of claim 12, wherein the annular cutting surfaces of each of the first and second scaffolds are configured to engage one another to resect the section of tissue.

15. The tissue resectioning apparatus of claim 12, each of the first scaffold and the second scaffold comprising:
   a main body having an inner surface and an outer surface, the inner surface circumscribing the central longitudinal axis, the main body comprising:
      a plurality of slots extending around a circumference of the main body; and
      a locking tab at an end of the main body, the locking tab extending through one of the plurality of slots to maintain the main body in a substantially tubular configuration; and
   a plurality of attachment tangs extending radially from the main body and from the central longitudinal axis, the plurality of attachment tangs operable to engage an interior wall of the section of tissue.

16. A method for tissue resectioning, the method comprising:
   inserting a tissue resectioning device into a gastrointestinal tract, the tissue resectioning device comprising:
      a first scaffold and a second scaffold, each of the first and second scaffolds having a substantially tubular configuration and annular cutting surfaces that oppose each other; and
      a hook tool engaged with at least one of the first scaffold and the second scaffold, the hook tool comprising a first plurality of hooks and a second plurality of hooks;
   engaging a target section of tissue of the gastrointestinal tract with the second plurality of hooks;
   moving the target section of tissue of the gastrointestinal tract inwards towards a central longitudinal axis of the tissue resectioning device, wherein the target section of tissue of the gastrointestinal tract is brought into a path of the annular cutting surfaces of each of the first and second scaffolds; and
   biasing, using the first plurality of hooks of the hook tool, the first scaffold and the second scaffold relative to one another to resect the target section of tissue of the gastrointestinal tract captured between the first scaffold and the second scaffold.

17. The method according to claim 16, further comprising:
   positioning the first scaffold along a first side of the target section of tissue of the gastrointestinal tract;
   positioning the second scaffold along a second side of the target section of tissue of the gastrointestinal tract, wherein the first scaffold and second scaffold are separated from one another by a gap;

engaging the first scaffold with the hook tool by inserting the hook tool through the first scaffold and the second scaffold; and moving the first scaffold towards the second scaffold using the hook tool to engage the target section of tissue of the gastrointestinal tract between the first scaffold and the second scaffold.

18. The method according to claim 16, further comprising securing the first and second scaffolds within the gastrointestinal tract using a plurality of attachment tangs extending radially from the tissue resectioning device.

19. The method according to claim 16, further comprising biasing the first scaffold relative to the second scaffold until the first scaffold overlaps with the second scaffold, wherein a diameter of the first scaffold is different than a diameter of the second scaffold.

* * * * *